United States Patent
Shannon

(10) Patent No.: US 7,184,963 B1
(45) Date of Patent: Feb. 27, 2007

(54) METHOD FOR DETERMINING CARE AND PREVENTION PATHWAYS FOR CLINICAL MANAGEMENT OF WOUNDS

(75) Inventor: Ronald J. Shannon, Washington Crossing, PA (US)

(73) Assignee: Bristol-Myers Squibb Company, New York, NY (US)

( * ) Notice: Subject to any disclaimer, the term of this patent is extended or adjusted under 35 U.S.C. 154(b) by 538 days.

(21) Appl. No.: 09/487,944

(22) Filed: Jan. 19, 2000

Related U.S. Application Data

(60) Provisional application No. 60/116,349, filed on Jan. 19, 1999.

(51) Int. Cl.
*H04N 9/491* (2006.01)

(52) U.S. Cl. .................. 705/2; 600/306; 600/557; 434/262

(58) Field of Classification Search .................. 705/1, 705/2, 3; 424/448; 514/12; 706/45; 600/31, 600/306, 557; 435/32; 128/859; 434/262
See application file for complete search history.

(56) References Cited

U.S. PATENT DOCUMENTS

| | | | |
|---|---|---|---|
| 4,799,500 A | 1/1989 | Newbury | 128/859 |
| 4,820,292 A | 4/1989 | Korol et al. | 435/32 |
| 5,265,605 A | 11/1993 | Afflerbach | 128/630 |
| 5,299,121 A | 3/1994 | Brill et al. | 364/413.01 |
| 5,505,943 A | 4/1996 | Fortney et al. | 424/94.63 |
| 5,517,405 A | 5/1996 | McAndrew et al. | 364/401 |
| 5,597,800 A | 1/1997 | Eibl et al. | 514/12 |
| 5,706,441 A | 1/1998 | Lockwood | 395/203 |
| 5,732,397 A | 3/1998 | DeTore et al. | 705/1 |
| 5,957,837 A | 9/1999 | Raab | 600/300 |

FOREIGN PATENT DOCUMENTS

WO  WO 03/084388 A2 * 10/2003

OTHER PUBLICATIONS

Instructions for Use, Pressure Sore Status Tool, *ConvaTec Brochure* (1990).
Bates-Jensen, et al., Validity and Reliability of the Pressure Sore Status Tool, *Decubitus,* vol. 5, No. 6, pp. 20-28 (1992).
Solutions, Wound Care Algorithm Series Flip Cards, *ConvaTec Brochure* (1998).

* cited by examiner

*Primary Examiner*—Raquel Alvarez
(74) *Attorney, Agent, or Firm*—John M. Kilcoyne

(57) ABSTRACT

The present invention relates to methods for consistently designating appropriate treatment protocols for patients, particularly protocols involving wounds or wound prevention. Specifically, the invention relates to methods wherein a patient condition such as a wound is assessed against defined scales for classifying and grading, which assessment is used in a visual decision tree device to identify one or more components of a treatment protocol.

10 Claims, 15 Drawing Sheets

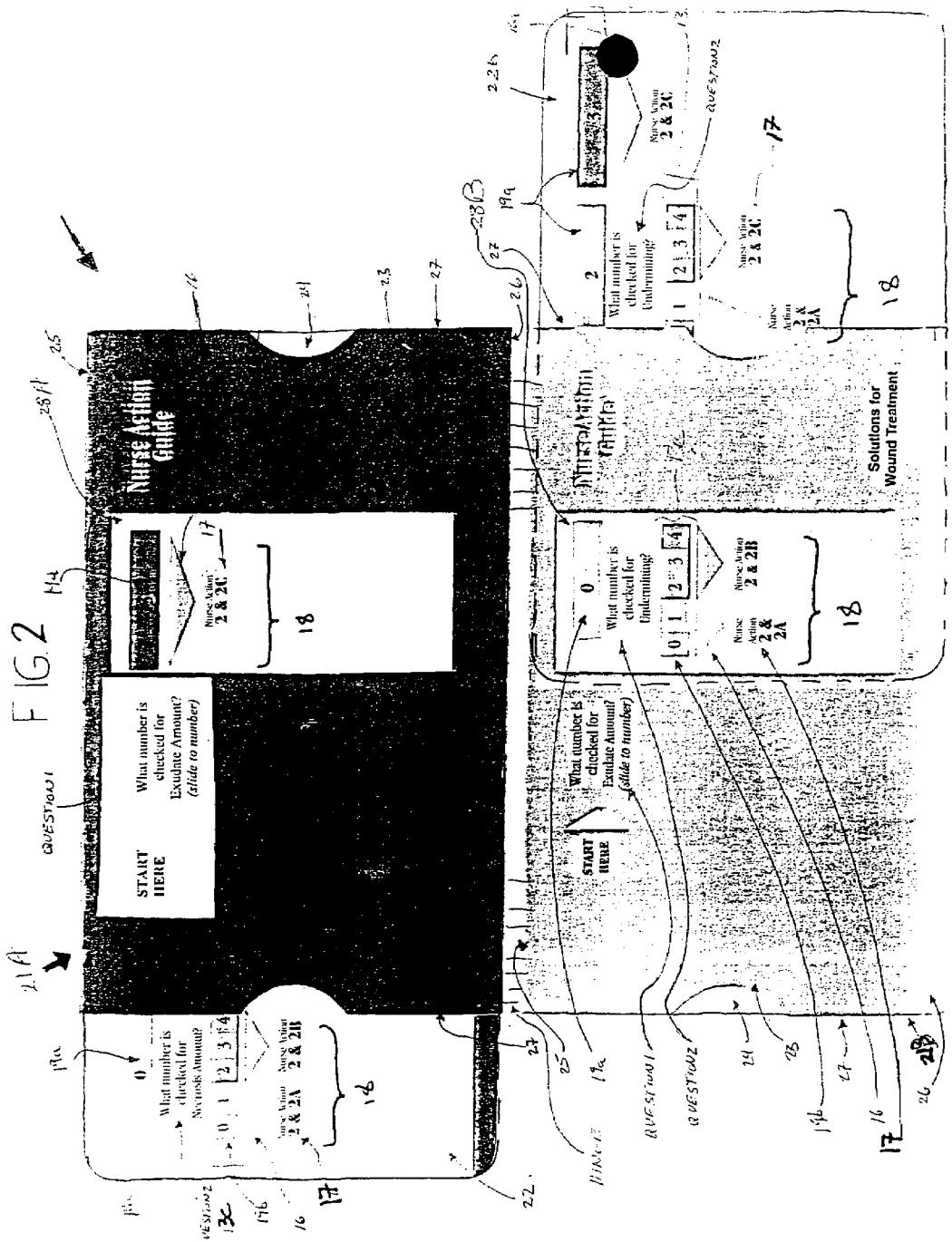

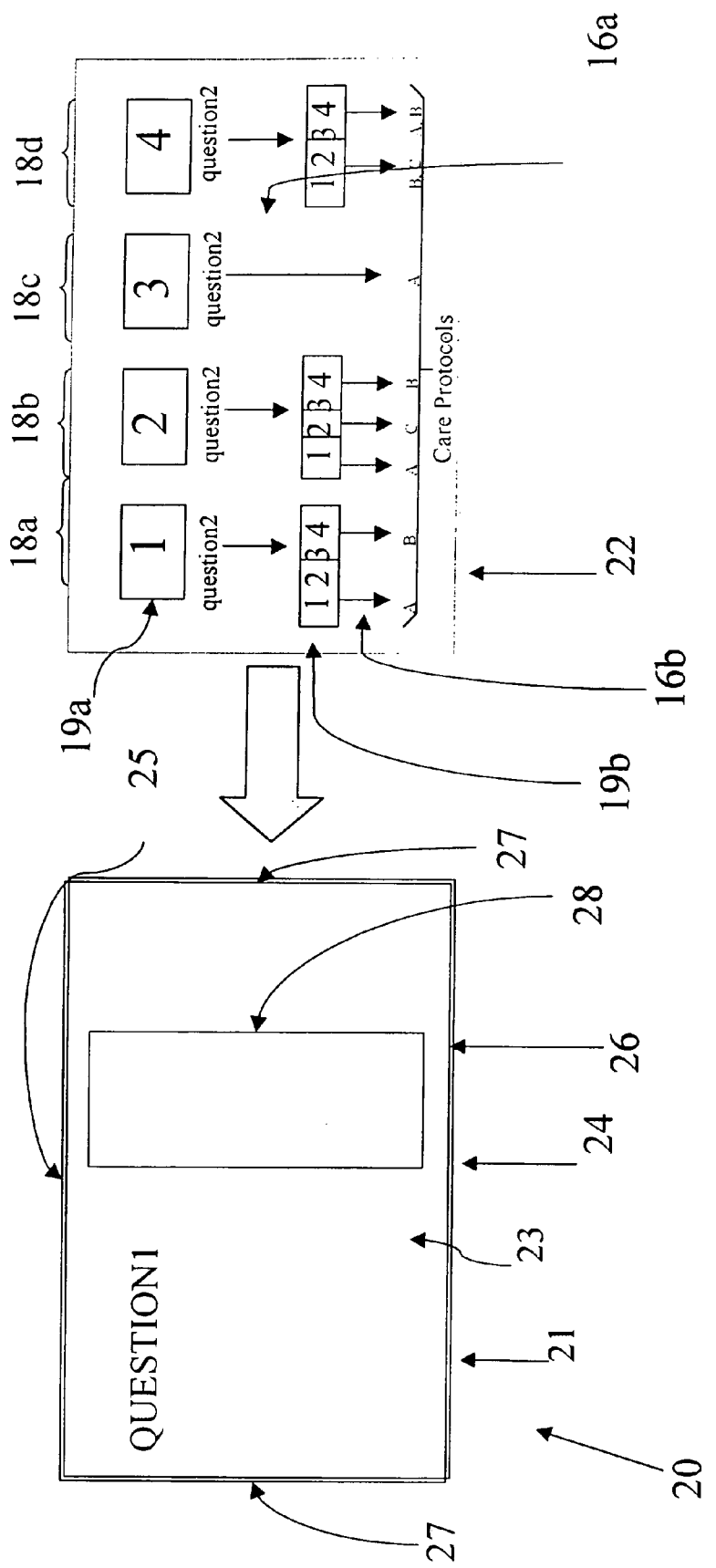

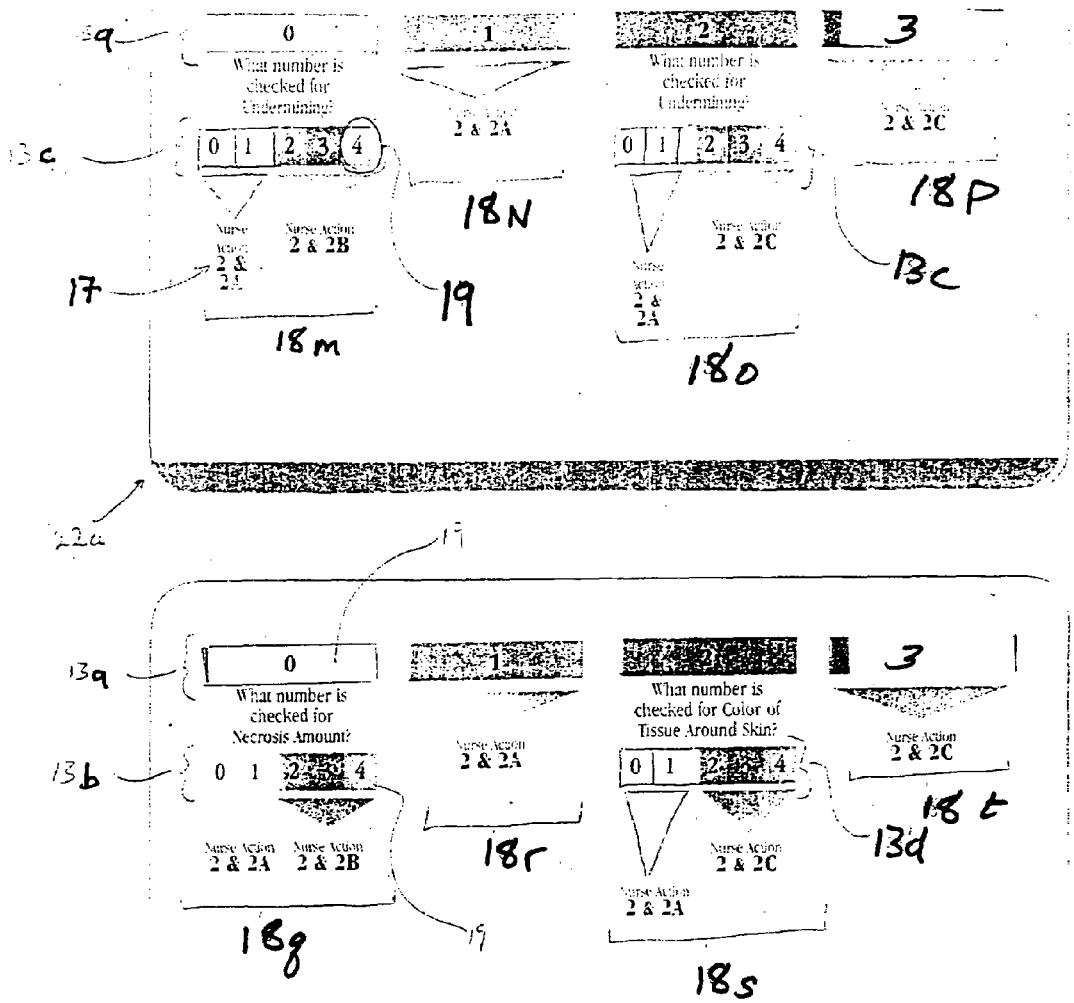

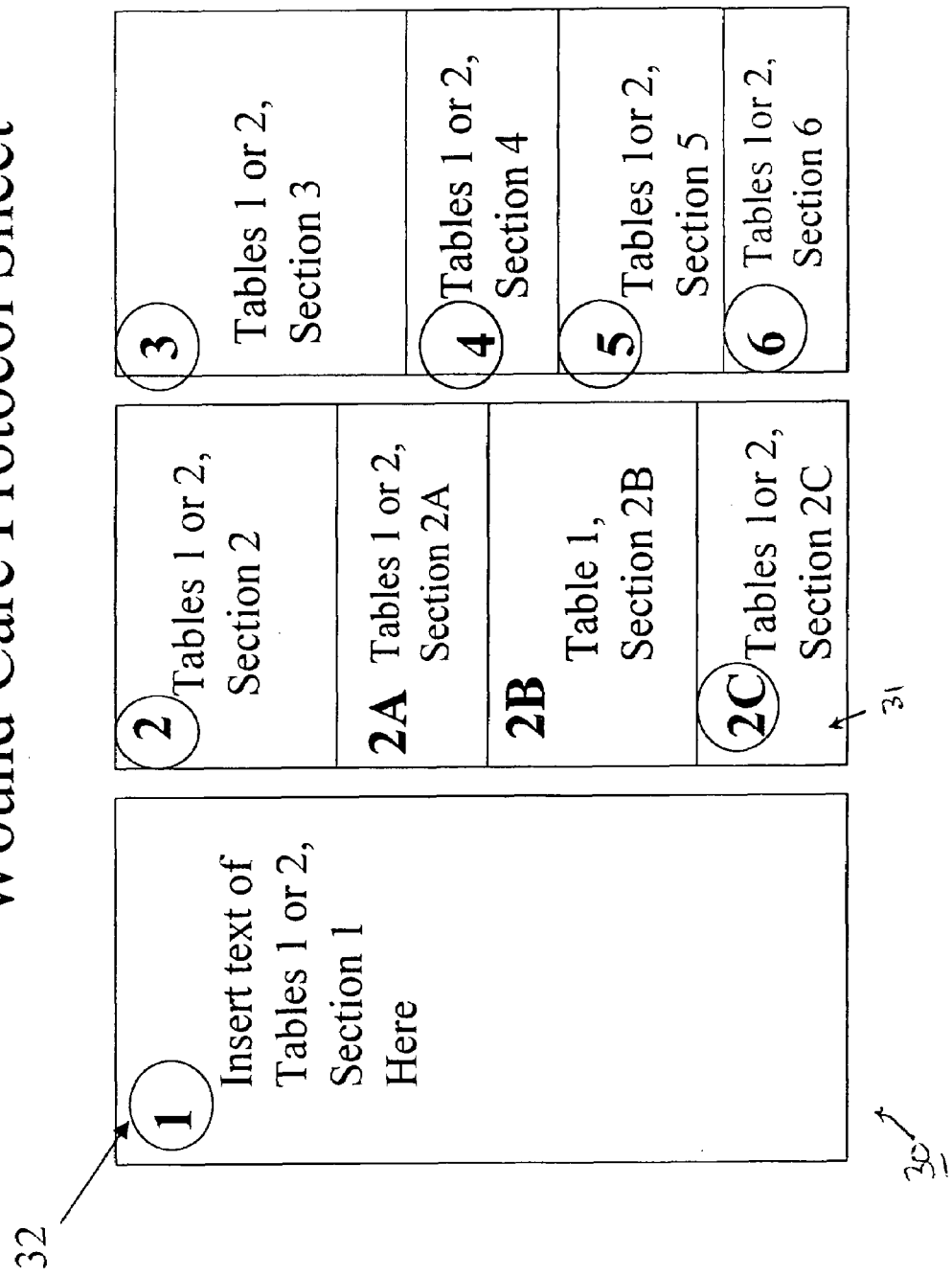
FIG. 3 Wound Care Protocol Sheet

FIG. 4

FIG 5D

FIG. 6
Nurse Action Report Sheet

| Managing Moisture | | Managing Moisture | | Managing Nutrition | | Friction & Shear | |
|---|---|---|---|---|---|---|---|
| A Table 3, Section 1A | E Table 3, Section 1E | G Table 3, Section 2G | K Table 3, Section 2K | O Table 3, Section 3O | | | |
| B Table 3, Section 1B | F Table 3, Section 1F | H Table 3, Section 2H | L Table 3, Section 2L | P Table 3, Section 3P | | W Table 3, Section 4W | |
| C Table 3, Section 1C | | I Table 3, Section 2I | M Table 3, Section 2M | Q Table 3, Section 3Q | | X Table 3, Section 4X | |
| D Table 3, Section 1D | | J Table 3, Section 2J | N Table 3, Section 2N | R Table 3, Section 3R | | | |
| | | | | S Table 3, Section 3S | | | |
| | | | | T Table 3, Section 3T | | | |
| | | | | U Table 3, Section 3U | | | |
| | | | | V Table 3, Section 3V | | | |

FIG. 7 Wound Care Assessment Record

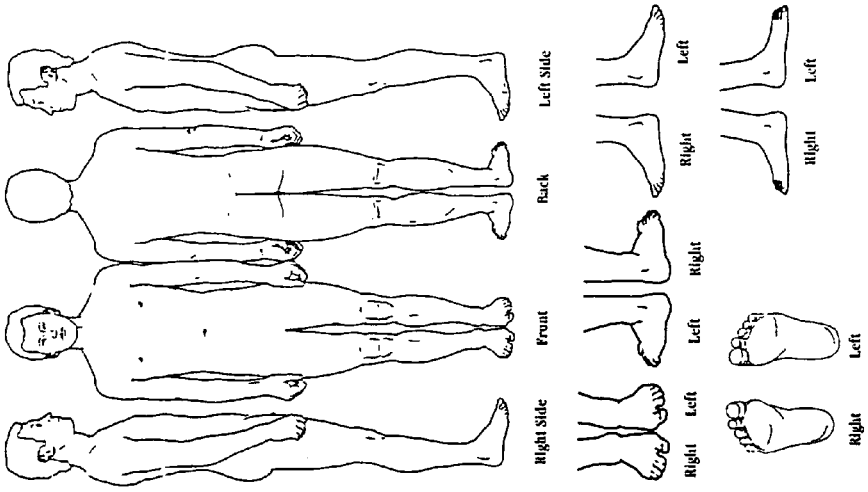

Name_____
Date of Birth_____ Admission Date:_____
Discharge Date:_____
Patient ID_____ Assessment Date_____
Existing Wound ☐ Ulcer #_____
New Wound ☐ Give Ulcer #_____
Clinician_____
Caregiver/Other

Measurements
*Length = Longest Axis*

Length _____ cm
Width _____ cm
Depth _____ cm

Butterfly Only
Length _____ cm
Width _____ cm
Length _____ cm
Width _____ cm
Depth _____ cm

Wound Type
☐ Arterial/Ischemic Ulcer
☐ Burn
☐ Neuropathic Ulcer
☐ Perineal
☐ Dermatitis
☐ Pressure Ulcer
☐ Rash
☐ Skin Tear
☐ Surgical Wound
☐ Venous Ulcer
☐ Other_____

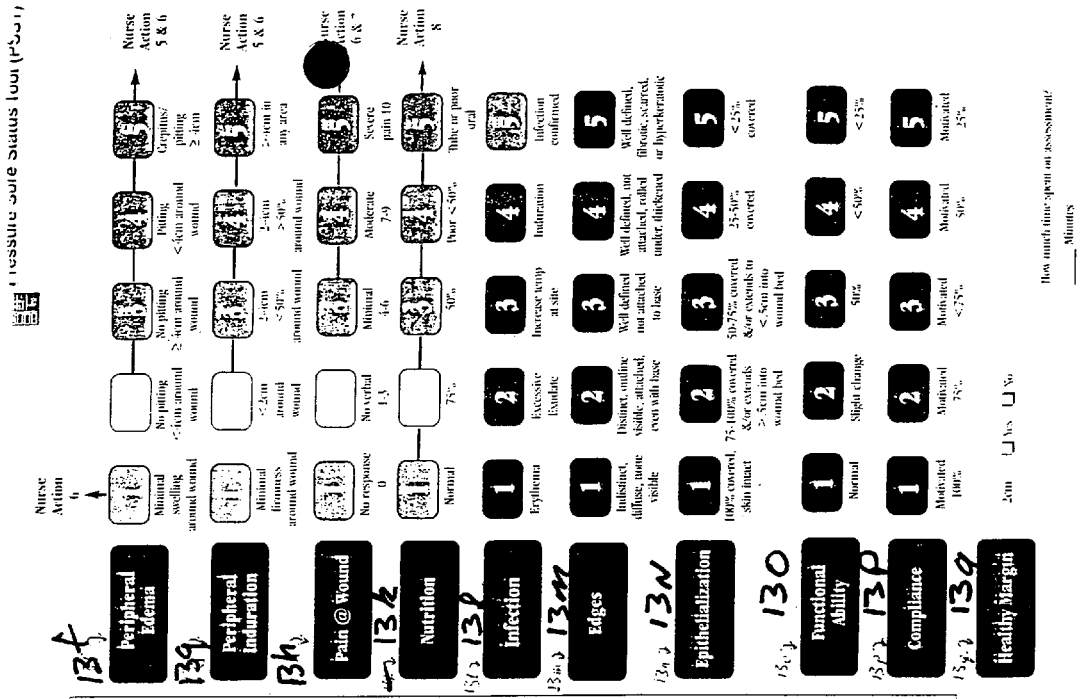

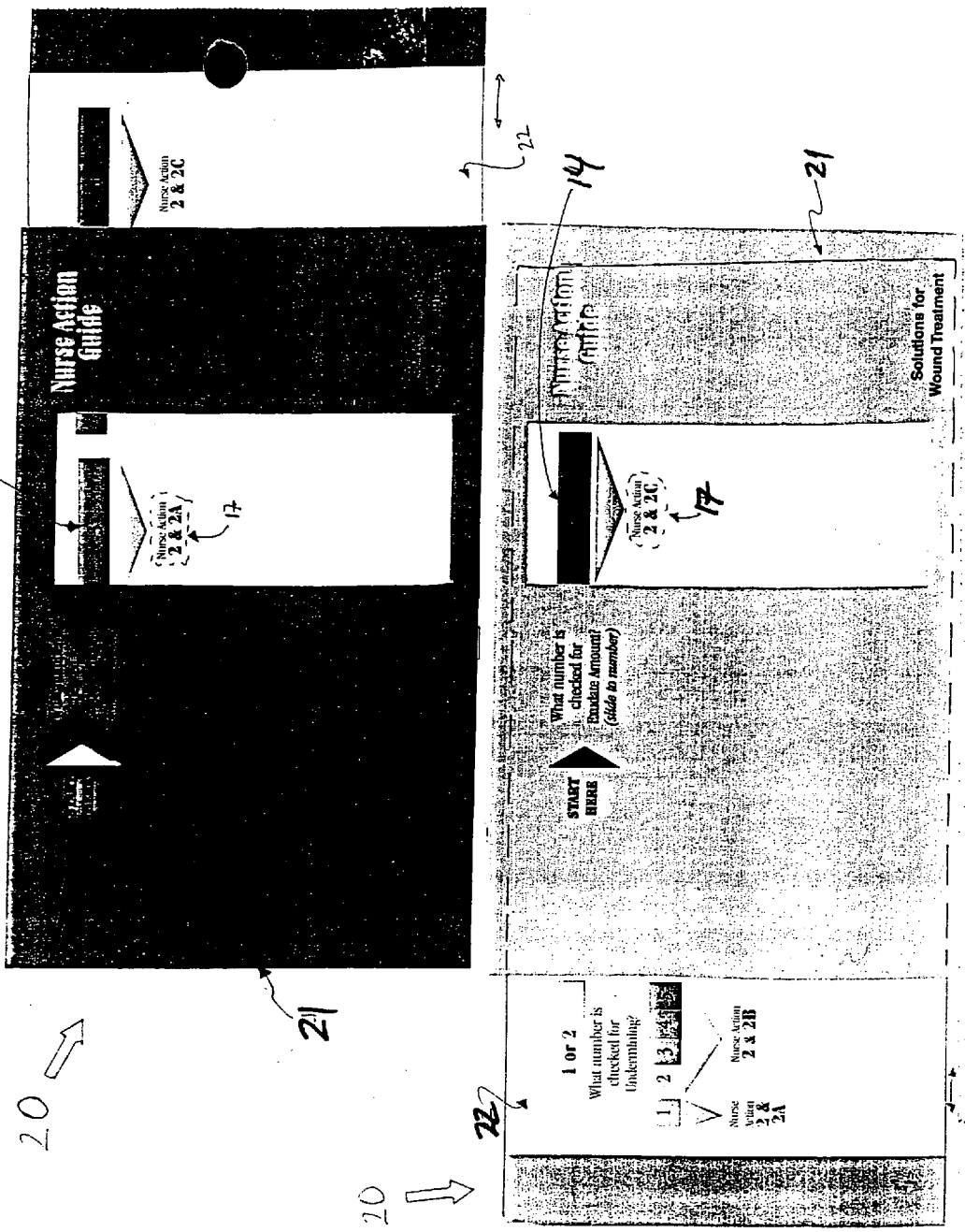

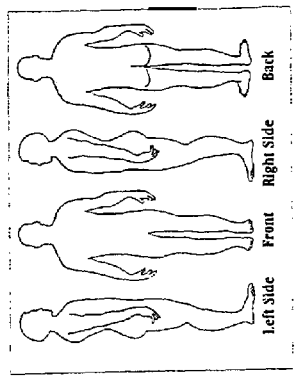

Indicate proper area

Left Side  Front  Right Side  Back

©1999 E.R. Squibb & Sons, Inc. Princeton, NJ

WSIS

Patient ID _____    Clinician _____
Assessment Date _____    Length/Width
Add New Wound _____    Ulcer # _____
Existing Wound _____

Status
☐ Active
☐ Healed

Wound Type
☐ Arterial/Ischemic Ulcer
☐ Burn
☐ Neuropathic Ulcer
☐ Perineal
☐ Dermatitis
☐ Pressure Ulcer
☐ Rash
☐ Skin Tear
☐ Surgical Wound
☐ Venous Ulcer
☐ Arterial/Ischemic Ulcer
☐ Other _____

Wound Shape
☐ Butterfly
☐ Irregular
☐ Linear/Elongated
☐ Oval
☐ Square
☐ Round
☐ Rectangle

Measurements
Length = Longest Axis
Length _____ cm
Width _____ cm
Depth _____ cm Butterfly Only
Length _____ cm
Width _____ cm
Length _____ cm
Width _____ cm
Depth _____ cm

Wound Stage
☐ Stage I
☐ Stage II
☐ Stage III
☐ Stage IV
☐ Unable to stage
☐ N/A

Wound Placement
☐ Left
☐ Right
☐ N/A

☐ Anterior
☐ Anterolateral
☐ Inferior
☐ Lateral
☐ Medial
☐ Posterior
☐ Other _____

Wound Site
☐ Ankle
☐ Back of Head
☐ Coccyx
☐ Ear
☐ Elbow
☐ Forearm
☐ Heel
☐ Iliac Crest
☐ Ischial Tuberosity
☐ Knee
☐ Lower Leg
☐ Sacrum
☐ Scapula
☐ Thigh
☐ Toe(s)
☐ Trochanter
☐ Vertebrae
☐ Other _____

Factors Delaying Wound Healing

Blood Related
☐ Anemia of any sort
☐ Compromised vascular tree (arterial, venous)

Malnutrition
☐ Albumin <3.0g/dl

Deficiencies in:
☐ Iron
☐ Protein
☐ Vitamin A
☐ Vitamin C
☐ Water
☐ Zinc

Metabolic Disorders
☐ Diabetes
☐ Thalassemia

Other
☐ Radiation Therapy/Cytotoxic Drugs
☐ Smoking
☐ Stress
☐ Steroids/Anti-Inflammatory Medications
☐ Surgery

Current Primary Diagnosis _____

— FIG 11 —

METHOD FOR DETERMINING CARE AND PREVENTION PATHWAYS FOR CLINICAL MANAGEMENT OF WOUNDS

This application is related to co-pending application No. 60/116,349 (filed Jan. 19, 1999), which is incorporated herein by reference in its entirety.

The present invention relates to methods for consistently designating appropriate treatment protocols for patients, particularly protocols involving wounds or wound prevention.

A number of computer programs have been developed wherein a user, for example a care giver, inputs parameters indicative of a patient assessment into a computer and obtains a care plan as an output. Input parameters can include art recognized assessment parameters, such as those recommended by the National Pressure Ulcer Advisory Board. One example of such a computer program is the Wound and Skin Intelligence System (WSIS) developed by Convatec and Applied Health Sciences. Other similar programs have been developed by Johnson & Johnson Medical (a division of Ethicon, Inc.) and Smith & Nephew, Ltd.

The effective use of such computer-based methods of deriving care plans often requires simultaneous proximity of the care giver to both the patient and the computer. Care givers without ready access to a patient in close proximity to the programmed computer cannot effectively benefit from such computer-based approaches. Moreover, even when the programmed computer is available, the practicalities of providing care often makes it awkward to input data prior to rendering a treatment protocol.

Accordingly, there is a need for a method of selecting care plans for patients customized to clinical assessment parameters that does not require immediate interaction with a computer, without compromising the quality of care provided. The present invention provides a method for correlating patient assessment parameters with appropriate treatment protocols. The method provides a visually keyed process to derive a care plan. The process does not require a computer, and when executed with a computer is highly integrated with visual cues. Such a process can be embodied in devices that provide bedside tools to assist the care giver to make evidence-based decisions for the care of individuals, such as individuals at risk of forming wounds or individuals who already have wounds, such as a pressure ulcers.

SUMMARY OF THE INVENTION

In one embodiment, the invention relates to a method of identifying a wound care protocol for a given wound or wound prevention protocol appropriate for a given patient comprising: classifying the wound or patient against a defined scale for a first wound factor, which is defined wound assessment factor or defined wound risk assessment factor to obtain a wound classification; grading the wound or patient against defined scales for one or more second wound factors, which are wound assessment factors or wound risk assessment factors; and operating a visual decision tree device to show a decision or visual decision tree corresponding to the wound classification or to a scale for a wound assessment factor, wherein the visual decision tree device identifies at least one component of a treatment protocol for the graded wound factors. In some embodiments, at least one visual decision tree indicates two or more distinct decisions based on the grade of one or more second wound factors. In some embodiments, the visual decision tree is a mechanical device. In some embodiments, the method can also comprise providing an interactive visual scoring sheet on which markers for the available scores for two or more wound factors are displayed; and marking the appropriate score for the two or more wound factors on the interactive visual scoring sheet, wherein the interactive visual scoring sheet contains a marker associated with one or more of the scores identifying an addition to the treatment protocol.

In some embodiments, the invention relates to a method comprising classifying the wound against a defined wound classification scheme; grading the wound against defined scales for one or more second wound assessment factors; and operating visual decision tree device to show a decision or visual decision tree corresponding to the wound classification or to a grade for a wound assessment factor, wherein at least one visual decision tree produced by the device dictates two or more distinct decisions based on the grade of one or more second wound assessment factors, and wherein the visual decision device identifies a treatment protocol for the wound classification and grades of the second wound assessment factors. In some embodiments of the invention, one of the two visual decision tree devices is selected based on wound classification, and the selected visual decision tree device is operated to show a decision or decision tree corresponding to a grade for exudate amount. In some embodiments, the wound classification scheme grades wounds from non-open or closed wounds, to wounds of various thicknesses, to wounds that cannot be graded due to obstructions.

The invention, in some embodiments, relates to a method of identifying a wound care protocol for a given wound or wound prevention protocol appropriate for a given patient comprising: classifying the wound or patient against a defined scale for a first wound factor, which is defined wound assessment factor or defined wound risk assessment factor to obtain a wound classification; grading the wound or patient against defined scales for one or more second wound factors, which are wound assessment factors or wound risk assessment factors; operating visual decision tree device to show the visual decision tree corresponding to the wound classification or to a scale for a wound assessment factor, wherein at least one visual decision tree dictates two or more distinct decisions based on the grade of one or more second wound factors, and wherein the visual decision tree device identifies at least one component of a treatment protocol for the graded wound factors; and marking a pre-defined display of treatment protocols to identify the components of a treatment protocol identified by the method. In some embodiments, the method of the invention is operated through a graphical user interface on an electronic processor, resulting in a display of treatment protocols that matches a printed display used in manual operations of the method.

The invention also relates to a visual decision tree device for identifying a wound care protocol for a given wound or wound prevention protocol appropriate for a given patient comprising: a mechanical or electronic device for identifying and displaying one of at least two decisions or visual decision trees based on one or more inputted wound factors according to a defined scale, wherein the visual decision tree device identifies at least one component of a treatment protocol for the graded wound factors. In some embodiments, the sliding card comprises markers corresponding to a defined scale for classifying the wound or patient. In some embodiments, one or more sliding cards shows a visual decision tree and wherein the housing comprises a view window through which one or more visual decision trees corresponding to the wound classification can be viewed. In some embodiments, the visual decision tree device is mechanical and wherein the slide card can be moved with respect to the housing to view through the view window any one of a plurality of individual decision trees displayed on the sliding card.

BRIEF DESCRIPTION OF THE DRAWINGS

FIG. 2 displays a chronic wound management decision tool, which is a type of portable mechanical slide-rule visual decision tree device.

FIG. 2A displays a schematic of a slide-rule visual decision tree device.

FIG. 2C shows a second set of two exemplary sliding cards.

FIG. 3 displays a schematic of a modular wound care protocol sheet.

Figure 4:
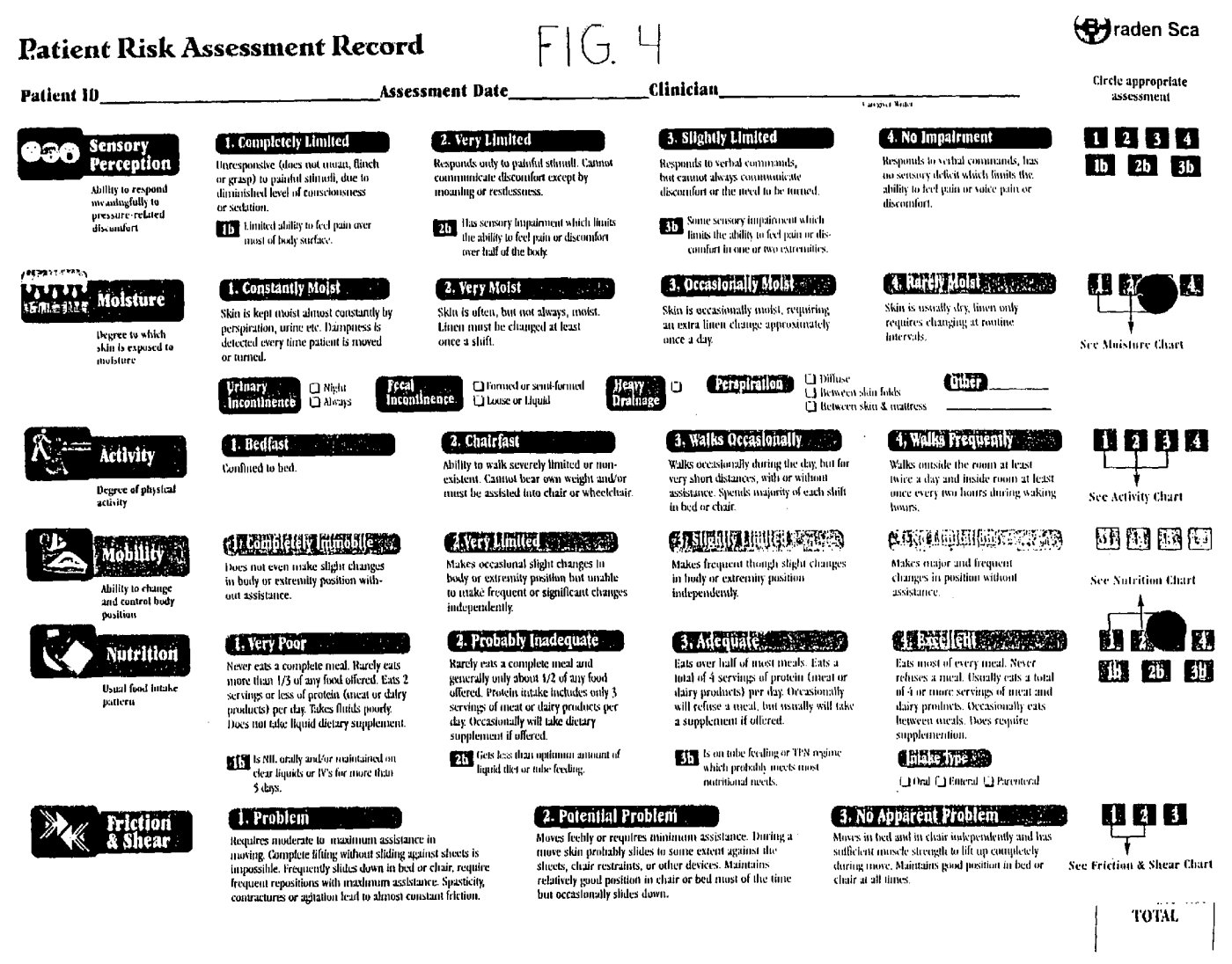

FIG. 4 displays a Patient Risk Assessment and Nurse Action Record, which is a type of interactive visual scoring sheet.

FIG. 5B displays a third set of two exemplary sliding cards.

FIG. 6 displays a modular wound prevention protocol sheet.

FIG. 7 displays a Wound Care and Assessment Record.

FIG. 9 displays a wound assessment interactive visual scoring sheet.

FIG. 10 displays a chronic wound management decision tool, which is a type of portable mechanical slide-rule visual decision tree device.

FIG. 11 displays a Wound Care and Assessment Record.

DETAILED DESCRIPTION OF THE INVENTION

Figure 1:
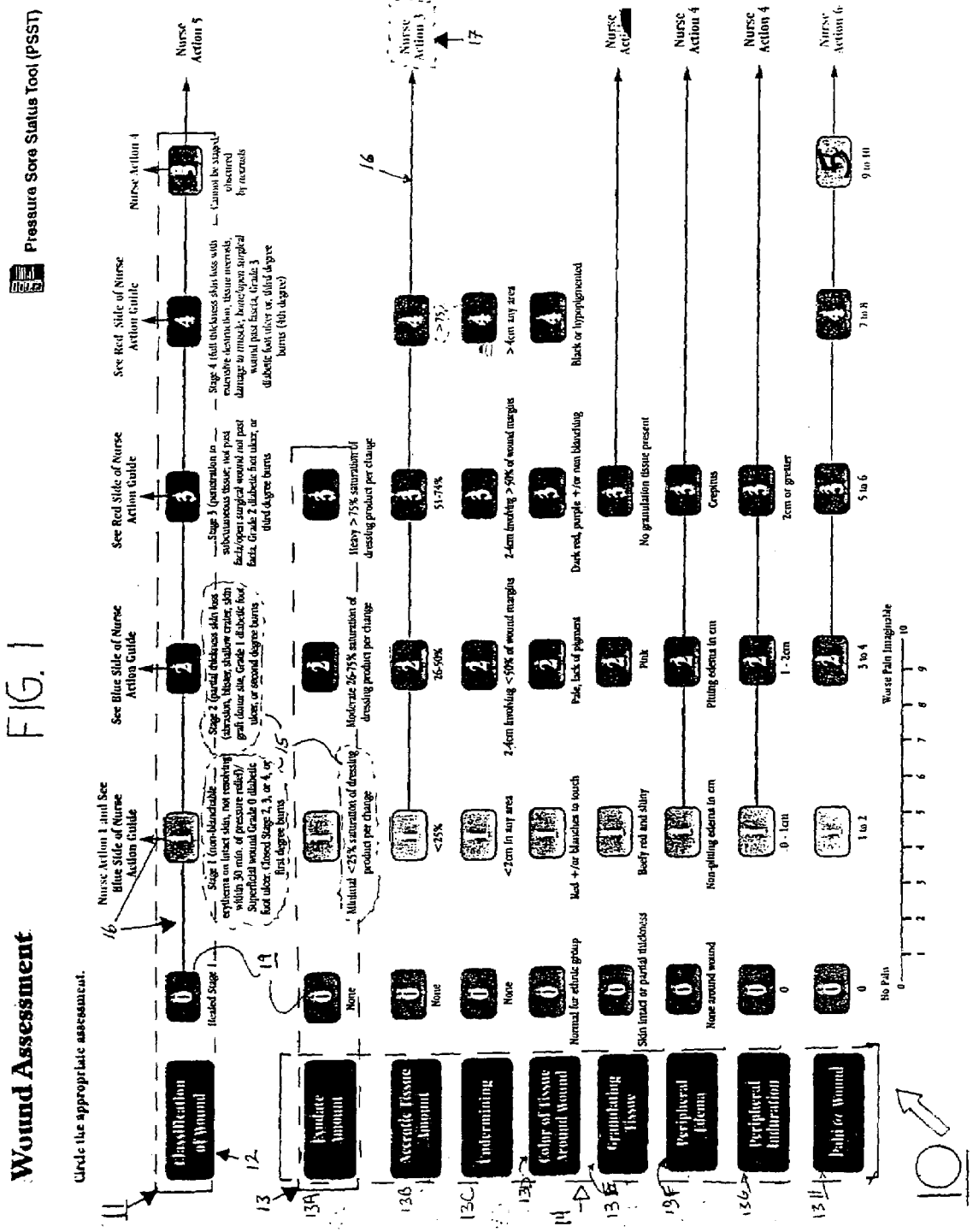
FIG. 1 displays a wound assessment interactive visual scoring sheet.

FIG. 1 relates to an interactive visual scoring sheet 10 that can be used according to a preferred embodiment of the present invention. The interactive visual scoring sheet 10 can take substantially the same visually-cued form on the screen of a computer or personal device assistant (PDA). In electronic form, each scoring choice is separately on a viewing screen represented as in the paper example illustrated in FIG. 1. The interactive visual scoring sheet 10 comprises a first defined scale 11 for classifying or grading a wound or patient according to a first wound factor 12 and a second defined scale 13 for classifying or grading the wound or patient for one or more second wound factors 14. In some embodiments, the second defined scale 13 can include classifying or grading of the wound or patient according to: a defined wound assessment factor, a defined wound risk assessment factor, some other classification of a patient's condition, or any combination of such factors. The first defined scale 11 and the second defined scale 13 can be represented by one or more markers 19 corresponding to one or more stages, grades or classifications. Markers 19 and associated criteria 15 can be indicated on the visual scoring sheet 10, for example, by indicia associated with markers 19, including varying colors, numbers, letters, symbols, texture or any combination thereof. Optional associated criteria is provide a brief indication of the classifying or grading criteria. In some embodiments, the appropriate score for one or more classifying or grading factors can be marked on the interactive visual scoring sheet 10. The criteria 15 can be indicated in whole or in part on the visual scoring sheet 10, or be referenced to criteria found elsewhere. The presence of at least a shorthand reference to the criteria is preferred. The second defined scales 13 can be with respect to one or more second wound factors 14. Second wound factors 14 can, in some embodiments, be selected from any number of factors including but not limited to: exudate amount, necrotic tissue amount, undermining, color of tissue around wound, granulating tissue, peripheral edema, peripheral induration and pain at wound. In some embodiments, second wound factors 14 can include, but are not limited to: sensory perception, moisture, activity, mobility, nutrition and friction & shear. In some embodiments, as shown in FIG. 9, first wound factors 12 and second wound factors 14 can be selected from the group consisting of: depth, exudate amount, exudate type, necrotic tissue amount, necrotic tissue type, undermining, surrounding skin color, granulation, peripheral edema, peripheral induration, pain at wound, nutrition, infection, edges, epithelization, functional ability, compliance and healthy margin.

The exemplary wound grading factors selected for FIG. 1 are a subset of the exemplary wound grading factors selected for FIG. 9. The selection of the particular factors of FIG. 1 as sufficient to predict patient care protocols represents an embodiment of the invention.

In some embodiments, one or more of the markers 19 for the first wound factor 12 or second wound factor 14 pertaining to a wound or patient condition can be connected by connecting indicia 16 such as lines or arrows that identify one or more treatment protocol components 17. One or more treatment protocol components 17 may be correlated to one or more markers 19, for example by connecting indicia 16, and may be written or referred to on the interactive visual scoring sheet 10.

The interactive visual scoring sheet 10 can form, include or be used in reference to a visual decision tree 18. Exemplary decision trees 18 are shown in FIG. 2. The visual decision tree 18 can comprise connecting indicia 16. The visual decision tree 18 can dictate two or more distinct decisions based on one or both of the first or second defined scales 11, 13 to identify a treatment protocol component 17 for the classified or graded factors. In FIG. 2, a first set of markers 19a on a first sliding card 22a are used to indicate values or stages of the first or second defined scales 11, 13. A second set of markers 19b are used on a second sliding card 22b to indicate values or stages of the first or second defined scales 11, 13 in the example illustrated in FIG. 2.

In some embodiments, the first defined scale 11 can grade wounds from non-open or closed wounds, to wounds of various thicknesses, to wounds that cannot be graded due to obstructions.

To assess a wound, the wound is first visually inspected and the particular wound or patient parameters are determined, for example, according to one or more defined scales for classifying or grading 11, 13. The wound or patient parameters can then be recorded by marking or indicating them on the interactive visual scoring sheet 10, for example by checking or circling appropriate markers 19. Connecting indicia 16 and a visual decision tree 18 can then be used to identify appropriate protocol components 17 corresponding to the indicated markers 19.

In one preferred embodiment of the invention depicted in FIG. 2, a visual decision tree device 20 is provided. A schematic of a visual decision tree device 20 is provided in FIG. 2A. In the nonlimiting example depicted in FIG. 2, the visual decision tree device 20 is a mechanical slide-rule device made up of a first housing 21A with a first view window 28A and a first sliding card 22a. Hingeably attached HINGE to the first housing 21A is second housing 21B into which slides a second sliding card 22b. The user inputs a value for one or more first 12 or second 14 wound factors according to the markers 19a, 19b for the first or second defined scales 11, 13 displayed on the first or second sliding cards 22a, 22b, for example by adjusting the position of the appropriate sliding card 22a or 22b within the appropriate housing 21A or 21B such that an appropriate marker 19a or 19b corresponding to the desired input value is displayed in view. Selection of the appropriate housing 21A or 21B and slide card 22a or 22b is determined in this example by connecting indicia 16 to the "Classification of Wound" score on the visual scoring sheet 10 of FIG. 1.

QUESTION 1 (FIG. 2A) identifies which first or second wound factor 12, 14 is used to identify the appropriate marker 19a. The display of the appropriate marker 19a aligns the appropriate decision or visual decision tree 18a–18d in the view window 28. If present, QUESTION 2 of the displayed visual decision tree identifies a marker 19b for which connecting indicia 16b identify appropriate wound care protocol components 17. In some instances, such as illustrated decision tree 18c, the decision tree identifies the wound care protocol component 17 from the marker 19a.

Wound care protocol components 17 can be grouped in modules on a wound care protocol sheet 30, as shown in FIG. 3. In some embodiments, protocol components 17 for wound care of wound prevention are grouped in alpha-numeric groups or modules 31 that correspond to decision tree 18 outcomes. Based on the decision tree 18 outcomes, one or more protocol components 17 may be followed. The modules 31 can be an alpha-numerically labeled module, can include goals for treatment, multiple alternative therapies and recommended products for treatment.

The schematic of FIG. 2A shows a two part visual decision tree devices 20 comprising a housing 21 and a sliding card 22. The housing can comprise a top layer 23 and a bottom layer 24 made of, for example, heavy paper or plastic, joined along a top edge 25 and a bottom edge 26. A view window 28 is cut into the top layer 23. In some embodiments (not shown in FIG. 2A), the view window can be cut into the top layer or the bottom layer. The sides of the top layer 23 and the bottom layer 24 are left open to allow the sliding card 22 to be inserted and moved within the housing 21. The top layer 23 can have a question QUESTION 1 printed on it, which governs where the operator should slide the sliding card 22 so that the appropriate marker from a first set of markers 19a is indicated in the view window 28. The sliding card 22 is slid within housing 21 to a position with respect to the view window 28 where the QUESTION 1 on the top layer 23 is correctly answered by an appropriate marker 19a. A first set of connecting indicia 16a (e.g. arrows) points to one or more values for a second set of markers 19b in response to QUESTION 2. The operator selects a value from the second set of markers 19b in response to a second question QUESTION 2 found on the sliding card 22 and performs the protocols (referenced as A, B or C in FIG. 2A at the bottom of the sliding card 22) that are indicated by a second set of arrows 16b.

Figure 2B:
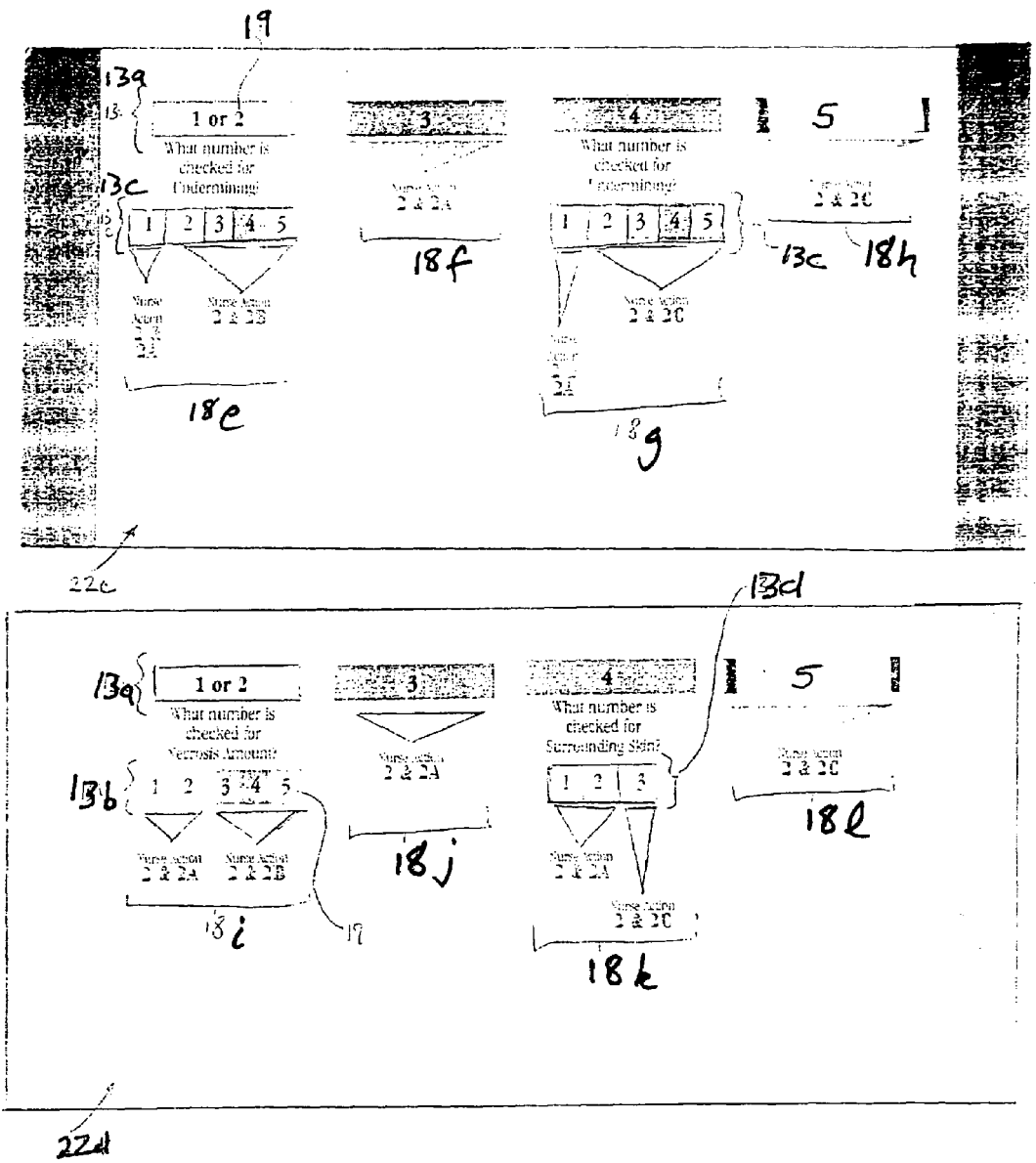
FIG. 2B displays a first set of two exemplary sliding cards.
Figure 5:
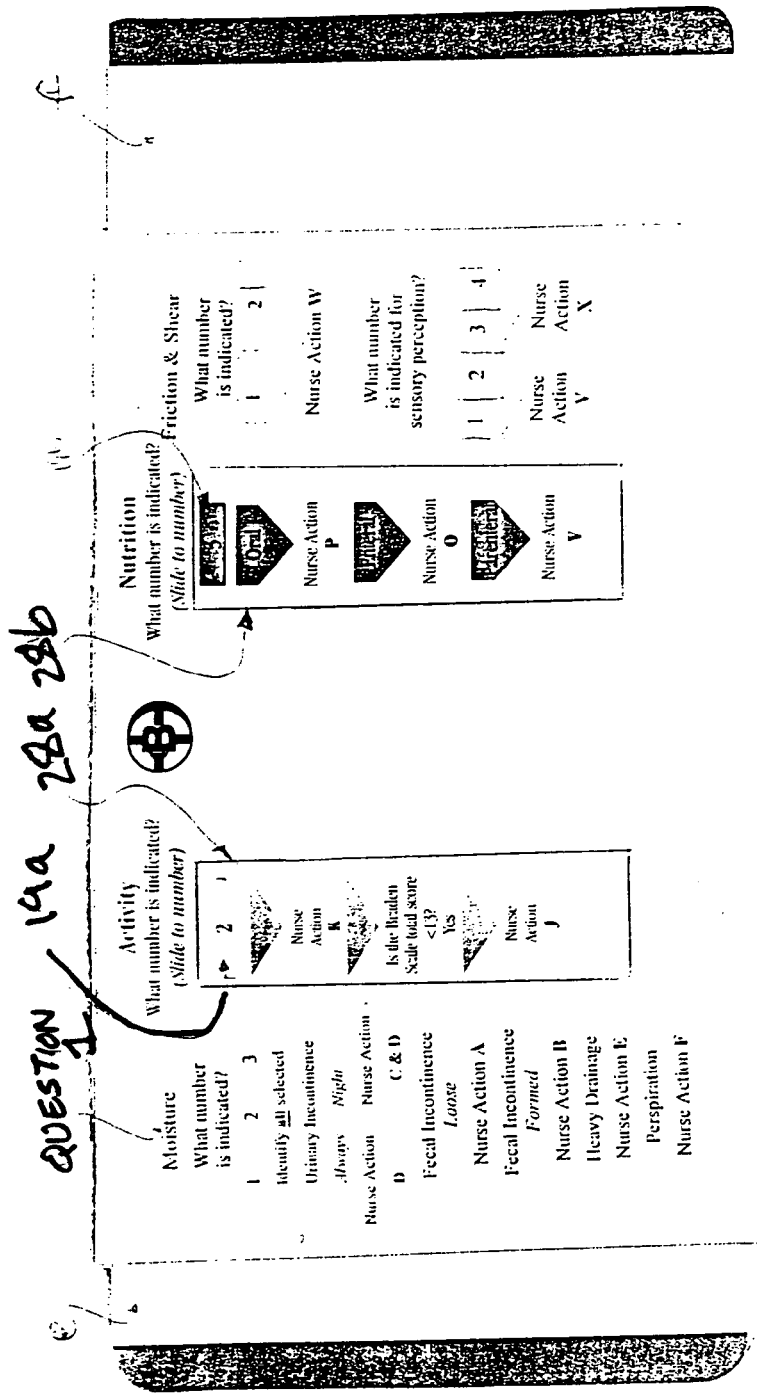
FIG. 5 displays a Patient Risk Assessment Evaluation Tool, which is a type of portable mechanical slide-rule decision tree device.
Figure 8:
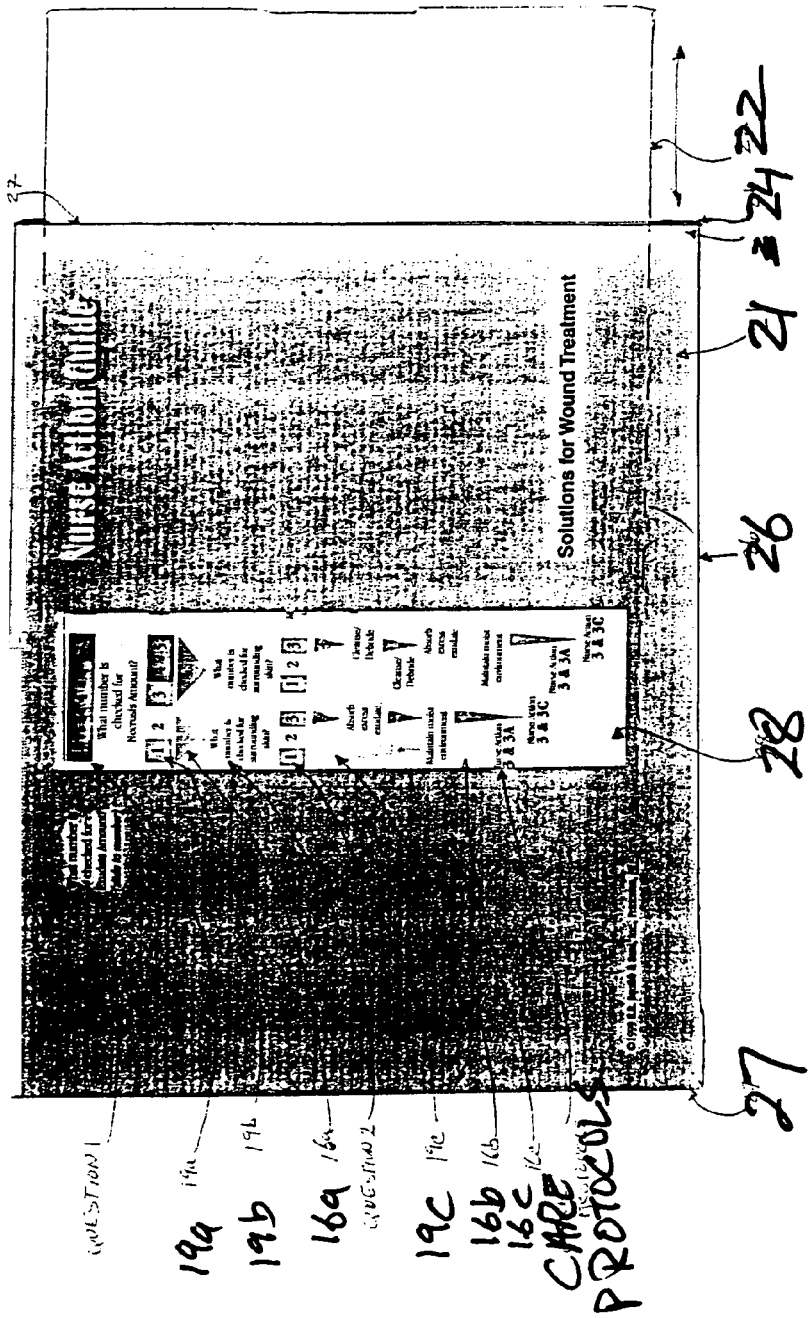
FIG. 8 displays a pressure ulcer pathway decision tool, which is a type of a portable mechanical slide-rule visual decision tree device.

In a particular example, the grade on first defined scale 11 on the interactive visual scoring sheet 10 of FIG. 1 identifies whether the slide rule of first housing 21A or the slide rule of second housing 21B shall be used (FIG. 2). Referring to second housing 21B of the visual decision tree device 20 of FIG. 2, the score for alpha second defined scale 13a identifies the position to which the ruler is adjusted. Referring to first and second sliding cards 22a, 22b of FIG. 2 and FIG. 2C, in the first sliding card 22a, one dialed position (e.g., "0" on defined scale 13a for first sliding card 22a of FIG. 2C) gives a wound care protocol component 17 depending on the score of beta second defined scale 13c. Another dialed position (e.g., "2" on defined scale 13a for second sliding card 22b of FIG. 2C) depends on the score of delta second defined scale 13d. Two dialed positions (e.g., "1" or "3" on defined scale 13a for first sliding card 22a of FIG. 2C) directly indicate wound care protocol components 17. Some dialed positions on the second sliding card depend on gamma second defined scale 13b. Referring to FIG. 1, additional wound care protocol components 17 are identified on the visual scoring sheet 10 by connecting indicia 16 associated with first defined scale 11 and beta, epsilon, zeta, eta and theta wound care protocol components 13B, 13E–13H (FIG. 1). Shown in FIGS. 2B and 2C are particular exemplary first slide and second slide cards 22c, 22d and 22a, 22b, (respectively). Some embodiments, for example as shown in FIG. 5 and FIG. 5B, can have a third sliding card 22e and a fourth sliding card 22f which can slide independently of each other to align a first marker 19a or a second marker 19b with a first view window 28a and a second view window 28b, respectively. These exemplary slide cards are shown in FIGS. 5B and 5C, respectively.

FIG. 2B and FIG. 2C display exemplary sets of first and second sliding cards 22a, 22b which can be used to practice the invention. The sliding cards 22a, 22b include separate visual decision trees 18e–18l that can be aligned with a view window of a housing. Likewise, FIG. 2C displays a set of first and second sliding cards 22a and 22b that include visual decision trees 18m–18t. For example, the first and second sliding cards 22c, 22d of FIG. 2B can be used in the visual decision tree device 20 of FIG. 10. Likewise, the first and second sliding cards 22a, 22b of FIG. 2C can be used in the visual decision tree device 20 of FIG. 2. In FIG. 2B, first and second sliding cards 22c, 22d have markers 19a that correspond to a first defined scale 13a and markers 19b that correspond to one or more second defined scales 13b, 13c, 13d. Similarly, first and second sliding cards 22a, 22b of FIG. 2C have a first set of markers 19a corresponding to a first defined scale 13a, a second defined scale 13b, a third defined scale 13c and a fourth defined scale 13d, which scales are defined for this example in the interactive visual scoring sheet 10 of FIG. 1. The example displayed in FIG. 2C can be used in the visual decision tree decice 20 of FIG. 2.

In preferred embodiments, a patient data sheet 40 can be combined with an interactive visual scoring sheet 10 and a wound care protocol sheet 30 in a patient care into a patient diagnostic tool which can be, for example, a single double sided folder or folded sheet of paper. The patient diagnostic tool can be used in conjunction with one or more visual decision tree devices 20.

The invention can comprise any number of embodiments, some of which are described in the Figures. In some embodiments of the invention, the interactive visual scoring sheet can have different first defined scale 11 and different second defined scale 12 for wound classifying or grading or patient risk assessment. FIG. 1, FIG. 4 and FIG. 9 show different visual scoring sheets 10 that can be used to practice the invention. FIG. 2, FIG. 5, FIG. 8 and FIG. 10 show different visual decision tree devices 20 that can be used to practice the invention. FIG. 3 and FIG. 6 show different wound care protocol sheets 30 that can be used to practice the invention. FIG. 7 and FIG. 11 show different patient data sheets 40 that can be used to practice the invention. The figures are provided as examples of possible embodiments of elements which may be used to practice the invention, and should not be construed to limit the scope of the invention.

Definitions

The following terms shall have, for the purposes of this application, the respective meaning set forth below.

interactive visual scoring sheet. An interactive visual scoring sheet is printed or electronic sheet on which scoring choices of wound factors are displayed in a form in which the scores can be visually marked.

matching electronic display. An electronic display of treatment protocols matches a traditionally printed display if the treatment options displayed match.

slide rule device. A mechanical visual decision tree device, which can include, for example, a slide rule or slide wheel device.

visual decision tree. A visual decision tree is a representation of two or more decisions, with the appropriate decision indicated visually based on the score of at least one wound factor.

visual decision tree device. A visual decision tree device is a device, electrical or mechanical, which can provide a visual image of a decision or decision tree based on an inputted wound care or wound prevention assessment value. The device produces two or more separate visual images of a decision or decision tree, including at least one decision tree depending on the input value. With a mechanical device, such as a slide rule or slide wheel, "inputting" comprises adjusting the mechanical device to correspond to the input value.

wound factor. A wound factor is a wound assessment factor for which there is a defined grading scale or a wound risk assessment factor for which there is a defined grading scale.

The following examples further illustrate the present invention, but of course, should not be construed as in any way limiting its scope.

EXAMPLE 1

Wound Treatment

One example of a method for assessing the status of a patient and derivation of a care plan, or protocol, for wound treatment is as follows. A front cover of a Wound Care & Assessment Record (FIG. 7) can be completed and included to identify the patient and care giver and to record dates and details of treatment, or the like. A Wound Assessment Record (Pressure Sore Status Tool), a type of interactive visual scoring sheet (FIG. 1) is completed by circling appropriate assessment scores for each factor (exudate amount, necrotic tissue amount, undermining, surrounding skin color, granulation, peripheral edema, peripheral induration, and pain). Using the interactive visual scoring sheet of FIG. 1, a care giver, upon examining a wound, classifies the wound as Stage 3 according to the first defined scale for classification. The care giver then assigns the following scores to assessing the wound according to their respective second defined scale for grading the wound: Exudate amount=3; Necrotic Tissue Amount=3; Undermining=2; Color of Tissue Around Wound=3; Granulating Tissue=3; Peripheral Edema=1; Peripheral Induration=0; Pain at Wound=4.

Next, the Chronic Wound Management Pathway Decision Tool, a type of portable mechanical slide-rule visual decision tree device, of FIG. 2 is used as follows: (i) using the Exudate Amount score selected from the interactive visual scoring sheet of FIG. 1, go to the colored side of the slide rule recommended; (ii) from the interactive visual scoring sheet of FIG. 1, identify the score checked for exudate amount and move the slide rule to the score for exudate amount; (iii) follow the arrows, answer all questions and select the appropriate nurse action items; (v) circle the numbers in the Nurse Action Report (Care Plan), a type of modular wound care protocol (FIG. 3).

Accordingly, the care giver having assessed the wound, follows the decision tree provided in FIG. 1 and FIG. 2 to arrive at a care plan from FIG. 3. Following the wound assessment data detailed in the above example, this process is as follows. First, the caregiver notes that the marker for Stage 3 in the Classification of Wound scale has two arrows connected to it: a vertical arrow (which points to "See Red Side of Nurse Action Guide") and a horizontal arrow that passes through the marker pointing from left to right (which points to "Nurse Action 5"). The vertical arrow requires the care giver to consult the red side of the decision tool (i.e. Nurse Action Guide), which corresponds to the top section of FIG. 2. Beginning at "START HERE" in the upper portion of the tool represented in FIG. 2, the care giver slides the card in the housing so that the number determined for Exudate Amount in the wound assessment is showing (i.e. "3" in the example). Once this is done, an arrow on the sliding card points to Nurse Actions 2 and 2C, which are found in FIG. 3, with accompanying text in Sections 2 and 2A of Table 1. The care giver then follows the protocols corresponding to Nurse Actions 2 and 2C.

Returning to the interactive visual scoring sheet of FIG. 1, the care giver next visually notes all factors indicated that are intersected by a line with an arrow attached as an endpoint (necrotic tissue amount, surrounding skin color, granulation, peripheral edema, peripheral induration, pain at wound and nutrition). If a line attached to the box is checked or circled then the care giver follows through to the end of the arrow where one finds the appropriate nurse action referenced. The care giver then records the nurse action on the modular wound care protocol (e.g., Nurse Action Report (Care Plan) of FIG. 3) by circling it. If a checked or circled box or marker does not have a line attached to it then the care giver is not required to do anything further for that marker. Finally, after circling all numbers on the modular wound care protocol (e.g. FIG. 3), the care giver follows the care plan and proceeds to take action.

Returning to the visual scoring sheet results in the above example, the horizontal arrow horizontally intersecting marker 3 for classification of wound and pointing to "Nurse Action 5" indicates that the care giver should also perform Nurse Action 5 (which is found in Section 5 of Table 1).

Next, the care giver can examine each marker indicated in the grading scales (from "Exudate Amount" down to "Pain @ Wound") and look for horizontal arrows passing through a marker. For instance, the marker for "3" indicated for "Necrotic Tissue Amount" has an arrow pointing to "Nurse Action 3". Accordingly, the care giver would then perform the protocol for Nurse Action 3 (found in FIG. 3, with text in Section 3 of Table 1). The results indicated above for "Granulating Tissue" (3) and "Peripheral Edema" (1) both require Nurse Action 4, however such multiple indications for any given Action do not increase the number of times the Action must be performed (i.e. in this example, Nurse Action 4 is performed once, not twice). Finally, the marker for "Pain @ Wound" (4) intersects an arrow that points to Nurse Action 6. Thus, in following the example above, the care giver would circle and perform Nurse Actions 2, 2C, 3, 4, and 5 as indicated in FIG. 3 by circles 32.

Table 1: Possible Text for Modular Wound Care Protocol Sheet (FIG. 3)

TABLE 1

| SECTION 1 | | |
|---|---|---|
| 1 | *GOAL* Maintain intact skin: Beware of deep tissue damage that may be irreversible. | |
| | Assess knowledge of patient/caregiver on risk of skin breakdown and methods of prevention. | ☐ Aloe Vesta 2-n-1 Skin Perineal/Skin Cleanser |
| | | Days Used M T W T F S S |
| | Reduce effect of risk factors. | ☐ Other_____ |
| | Pressure: regular repositioning and pressure distribution (pillows, devices) | Days Used M T W T F S S |
| | | Moisture Barriers |
| | Shear/friction: Apply protective ointment or moisture retentive dressing to reduce friction | ☐ Aloe Vesta 2-n-1 Protective Ointment |
| | | Days Used M T W T F S S |
| | | ☐ Sensi-Care Protective Barrier |
| | Excess Moisture: Clean at routine intervals with a skin cleanser, pat dry. | Days Used M T W T F S S |
| | | ☐ Other_____ |
| | Protect skin from moisture and irritants with a moisture barrier and/or absorbent dressings/absorbent products. | Days Used M T W T F S S |
| | | Skin Moisturizers |
| | | ☐ Aloe Vesta 2-n-1 Skin Conditioner |
| | Dryness: Follow routine bathing procedure with gentle cleansers. | Days Used M T W T F S S |
| | | ☐ Sensi-Care Protective Barrier |
| | Moisturize immediately after bathing. Apply body cream for areas prone to extreme dryness. | Days Used M T W T F S S |
| | | ☐ Other_____ |
| | | Days Used M T W T F S S |
| | Trauma/Skin Tears: Apply protective coverings to protect against friction and/or pressure | Moisture Retentive Dressings |
| | | ☐ DuoDERM Extra Thin    Size____ |
| | | Days Used M T W T F S S |
| | Nutrition altered: Nutritional Support Action Taken_____ | Absorbent Dressings |
| | | ☐ Lyofoam    Size____ |
| | _____ | Days Used M T W T F S S |
| | SKIN CARE PRODUCTS: | ☐ Hydrosorb    Size____ |
| | Patient Bathing | Days Used M T W T F S S |
| | ☐ Aloe Vesta 2-n-1 Body Wash/Shampoo | ☐ Other_____    Size____ |
| | Days Used M T W T F S S | Days Used M T W T F S S |
| | ☐ Sensi-Care Perineal/Skin Cleanser | Protective Coverings |
| | Days Used M T W T F S S | ☐ Tubifast |
| | | Days Used M T W T F S S |
| | | ☐ Tubipad |
| | | Days Used M T W T F S S |
| | | ☐ Arthropad |
| | | Days Used M T W T F S S |
| | | ☐ Other_____ |
| | | Days Used M T W T F S S |
| SECTION 2 | | |
| 2 | *GOAL* Obtain a clean wound bed. | 2C *GOAL* Absorb excess exudate/ maintain moist wound environment. |
| | PRODUCTS: | PRODUCTS: |
| | Wound Cleansing | Primary Dressing |
| | ☐ SAF Clens | Exudate Management |
| | Days Used M T W T F S S | ☐ AQUAGEL Hydrofiber    Size____ |
| | ☐ Other_____ | Days Used M T W T F S S |
| | Days Used M T W T F S S | ☐ Kaltostat    Size____ |
| | 2A *GOAL* Provide moist wound environment. | Days Used M T W T F S S |
| | | ☐ Lyofoam Foam Dressing  Size____ |
| | PRODUCTS: | Days Used M T W T F S S |
| | Primary Dressing | ☐ Other_____ |
| | Moisture Retentive Dressing | Days Used M T W T F S S |
| | ☐ DuoDERM CGF  Size____ | Secondary Dressing |
| | Days Used M T W T F S S | Moisture Retentive Dressing |
| | ☐ Other_____    Size____ | ☐ DuoDERM CGF    Size____ |

TABLE 1-continued

| | |
|---|---|
| Days Used M T W T F S S | Days Used M T W T F S S |
| Secondary Dressing   Not applicable. | ☐ Other_____   Size___ |
| | Days Used M T W T F S S |
| | PRODUCTS: |
| 2B *GOAL* Assist in autolytic debridement and removal of necrotic tissue/ | |
| Provide moist wound environment. | |
| PRODUCTS: | Secondary Dressing |
| Primary Dressing | Moisture Retentive Dressing |
| Wound Hydration | ☐ DuoDERM CGF   Size___ |
| ☐ DuoDERM Hydroactive Gel | Days Used M T W T F S S |
| Days Used M T W T F S S | ☐ Other_____   Size___ |
| ☐ Other_____ | Days Used M T W T F S S |
| Days Used M T W T F S S | |

SECTIONS 3 AND 4

3  *GOAL* Reduce devitalized tissue.
PRODUCTS:
Debridement
The suggested topical treatments will facilitate autolytic debridement. Autolytic debridement is usually not recommended for patients with infected wounds or patients at increased risk of infection.
☐ Surgical by   ☐ MD   ☐ Nurse   ☐ Enzymatic
Days Used M T W T F S S
☐ Autolytic   ☐ Mechanical
Products Used
_____
_____

| | |
|---|---|
| 4  *GOAL* Identify infection and institute medicine treatment. | |
| If infection is confirmed, perform Nurse | PRODUCTS: |
| Action 4A. If infection is not confirmed, | Primary Dressing |
| perform Nurse Action 4B. | Wound Hydration |
| Nurse Action 4A: Appropriate medical | ☐ DuoDERM Hydroactive Gel |
| treatment for infection should be initiated or | Days Used M T W T F S S |
| continued. DuoDERM CGF dressings can be | ☐ Other_____ |
| continued during the treatment of infection | Days Used M T W T F S S |
| at the discretion of the clinician. | Secondary Dressing |
| Nurse Action 4B: Evaluate for signs of | Moisture Retentive Dressing |
| infection. If not infected, moisture retentive | ☐ DuoDERM CGF   Size___ |
| dressing should extend beyond reddened | Days Used M T W T F S S |
| area to protect skin. | ☐ Other_____   Size___ |
| Minimize friction and shear forces to | Days Used M T W T F S S |
| surrounding skin. | |
| Action Taken and Products Used to Treat | |
| Infection_____ | |
| _____ | |

SECTIONS 5 AND 6

| | |
|---|---|
| 5  *GOAL* .Prevent further skin breakdown and stimulate healing. | |
| Relieve pressure | ☐ Bed/Mattresses_____ |
| PRESSURE ULCER | ☐ Devices_____ |
| --institute turning schedule for patient | ☐ Other_____ |
| --utilize pressure reduction device(s) | |
| Action Taken and Products Used | |
| _____ | |
| _____ | |
| VENOUS STASIS ULCER | PRODUCTS: |
| Compression Therapy | ☐ SurePress ™ High Compression Bandage |
| (30–40 mm/Hg pressure to heal ulcer) | ☐ SurePress Absorbent Padding |
| | ☐ UNNA-FLEX |
| | Days Used M T W T F S S |
| DIABETIC FOOT ULCERS | Action Taken and Products Used |
| Off loading of pressure | |
| | _____ |
| | _____ |

6  *GOAL* Pain Management
Provide analgesics. Cover with Moisture Retentive Dressings.
Action Taken and Products Used
_____
_____

Table 2: Possible Text for Modular Wound Care Protocol Sheet (FIG. 3)

Solutions for Would Treatment

Nurse Action Report (Care Plan) Circle or check off the appropriate treatments and indicated products used.

TABLE 2

SECTION 1

1  *GOAL* Maintain intact skin: Beware of deep tissue damage that may be irreversible.

| | |
|---|---|
| Assess knowledge of patient/caregiver on risk of skin breakdown and methods of prevention. | PRODUCTS: Patient Bathing |
| | ☐ Aloe Vesta Body Wash/Shampoo |
| Reduce effect of risk factors. | Days Used M T W T F S S |
| Pressure: regular repositioning and pressure distribution (pillows, devices) | ☐ Septi-soft Body Wash/Shampoo Days Used M T W T F S S |
| Shear/friction: Apply Skin Care products (lubricate) or Moisture Retentive Dressing (reduce friction) | ☐ Other_____ Days Used M T W T F S S Skin Protection |
| Excess Moisture: Manage with Skin Care Products or Moisture Retentive Dressing (protection) and incontinence products | ☐ Aloe Vesta Skin Cream Days Used M T W T F S S ☐ Aloe Vesta Protective Ointment |
| Dryness: Use Skin Care bathing and protection products. | Days Used M T W T F S S ☐ Other_____ |
| Nutrition altered: Nutritional Support Action Taken_____ | Days Used M T W T F S S Incontinence Care |
| | ☐ Aloe Vesta Antifungal Ointment |
| | Days Used M T W T F S S |
| | ☐ Aloe Vesta Protective Ointment |
| | Days Used M T W T F S S |
| | ☐ Aloe Vesta Perineal Foam |
| | Days Used M T W T F S S |
| | ☐ Aloe Vesta Perineal Solution |
| | Days Used M T W T F S S |
| | ☐ Ilex Skin Protectant Paste |
| | Days Used M T W T F S S |
| | ☐ Other_____ |
| | Days Used M T W T F S S |

SECTIONS 2 and 3-Debride Necrotic Tissue

2  Debride necrotic tissue.
3  *GOAL* Provide systematic support/preventive measures to facilitate healing based on general patient assessment findings

| | |
|---|---|
| 3  Wound Cleansing. | 3A  Moisture Retention |
| PRODUCTS: | Primary Dressing: |
| ☐ Saline | PRODUCTS: |
| Days Used M T W T F S S | ☐ DuoDERM CGF |
| ☐ SAF Clens | Days Used M T W T F S S |
| Days Used M T W T F S S | ☐ DuoDERM Extra Thin |
| ☐ Other | Days Used M T W T F S S |
| Days Used M T W T F S S | ☐ Signadress |
| | Days Used M T W T F S S |
| | ☐ Other |
| | Days Used M T W T F S S |
| | Secondary Dressing: N/A |
| 3B  Wound Hydration | 3C  Exudate Management |
| Primary Dressing: Wound Hydration: | Primary Dressing: Exudate Management: |
| PRODUCTS: | PRODUCTS: |
| ☐ DuoDERM Hydroactive CGF | ☐ Aquacel Hydrofiber |
| Days Used M T W T F S S | Days Used M T W T F S S |
| ☐ SAF Gel | ☐ Kaltostat Dressing |
| Days Used M T W T F S S | Days Used M T W T F S S |
| ☐ Other | ☐ Carboflex Odor |
| Days Used M T W T F S S | Days Used M T W T F S S |
| Secondary Dressing: Moisture Retentive Dressing: | ☐ Other Days Used M T W T F S S |
| PRODUCTS: | Secondary Dressing: |
| ☐ DuoDERM CGF | Moisture Retentive Dressing: |
| Days Used M T W T F S S | PRODUCTS: |
| ☐ DuoDERM Extra Thin | ☐ DuoDERM CGF |
| Days Used M T W T F S S | Days Used M T W T F S S |
| ☐ Signadress | ☐ DuoDERM Extra Thin |
| Days Used M T W T F S S | Days Used M T W T F S S |
| ☐ Other | ☐ Signadress |
| Days Used M T W T F S S | Days Used M T W T F S S |
| | ☐ Other |
| | Days Used M T W T F S S |

TABLE 2-continued

SECTIONS 4, 5, 6, and 7

4   *GOAL* Reduce devitalized tissue.
Debridement: The suggested topical treatments will facilitate autolytic debridement.
Autolytic debridement is usually not recommended for patients with infected wounds or
patients at increased risk of infection.
☐ Surgical by  ☐ MD  ☐ Nurse  ☐ Enzymatic
Days Used M T W T F S S
☐ Autolytic  ☐ Mechanical
Products Used
_____
_____

5   If infection is confirmed, perform Nurse Action 5A. If infection is not confirmed,
    perform Nurse Action 5B.

| 5A | 5B |
|---|---|
| Appropriate medical treatment for infection should be initiated or continued. DuoDERM CFG dressings can be continued during the treatment of infection at the discretion of the clinician. | Evaluate for signs of infection. If not infected, moisture retentive dressing should extend beyond reddened area to protect skin. Minimize friction and shear forces to surrounding skin. |
| Action Taken and Products Used to Treat Infection | |

| 6  Relieve Pressure | 7  Provide analgesics. Cover with Moisture Retentive Dressings. |
|---|---|
| Action Taken and Products Used | Action Taken and Products Used |

SECTION 7

8
| Has the patient been screened for nutritional deficiency indicators in the past month. | ☐ Functional limitations |
|---|---|
| | ☐ Chewing/swallowing |
| | ☐ Mobility |
| ☐ No  Yes → Rescreen | ☐ Hearing/speech |
| ⇓            Monthly | ☐ Vision |
| Evaluate the patient for presence of any | ☐ Dexterity |
| of the following nutritional deficiency | ☐ Altered mental state ☐ Medical Condition |
| indicators. | ☐ Diabetes |
| ☐ Elderly | ☐ Arterial Insufficiency |
| ☐ Infection | ☐ Cardiovascular disease |
| ☐ Wound | ☐ Venous Insufficiency |
| ☐ Systemic | ☐ Incontinence |
| ☐ Other_____ | ☐ Gastrointestinal disorder |
| ☐ Score of <18 on Braden Scale | ☐ Immunosuppression |
| ☐ Poor response to current would treatment for past 2–4 weeks | ☐ Drug Therapy |
| | ☐ Corticosteroids |
| ☐ Recent unintentional weight loss/gain | ☐ Immunosuppressants |
| | ☐ Antitumor agents |
| If any of the above is checked, perform Nutrition Assessment. | |

EXAMPLE 2

Wound Prevention

One example of a method for assessing the status of a patient and derivation of a care plan, or protocol, for wound prevention is as follows. A Patient Risk Assessment Evaluation Sheet (FIG. 4), a type of interactive visual scoring sheet, is completed by a care giver using a variation of the Braden Scale by circling appropriate assessment scores for each risk factor (sensory perception, moisture, activity, mobility, nutrition and friction & shear). Second, the Slide Rule Pressure Ulcer Pathway Decision Tool of FIG. 5 is used as follows: the slide rule is moved to each respective checked score from the Patient Risk Assessment Record (FIG. 4) for each respective risk factor. The arrows downward in the slide rule are followed to select the nurse actions (letters A to X) that correspond with the information contained in the Patient Risk Assessment Record. Finally, all letters in the a modular wound prevention protocol sheet (also called a Nurse Action Report, FIG. 6) selected from the slide rule are circled. Circled protocols are then followed. Table 3 provides the text of protocols that can be arranged on a single wound prevention protocol sheet, as shown schematically in FIG. 6.

The method of practicing the invention is outlined in the example below. The care giver obtains the Patient Risk Assessment Record (FIG. 4) and the Slide Rule Pressure Ulcer Pathway Decision Tool of FIG. 5, and then examines a patient. The care giver obtains the following assessments: Sensory Perception=3; Moisture=1; Activity=2; Mobility=2; Nutrition=4; Friction & Shear=3. After recording this assessment on the Patient Risk Assessment Record (FIG. 4), the care giver follows any arrows in FIG. 4. Specifically, the Moisture grading of 1 points to "See Moisture Chart", the Activity grading of 2 points to "See Activity Chart", the Nurtition grading of 4 has no arrows and the Friction & Shear grading of 3 has no arrows.

The care giver the uses the Slide Rule Pressure Ulcer Pathway Decision Tool of FIG. 5, and follows the decision tree for moisture. The first and second sliding cards 22e, 22f of FIG. 5 are displayed in FIG. 5B. Answering all questions, the care giver performs all nurse actions that apply. For instance, if the patient does not suffer urinary or fecal incontinence, but does perspire the care giver would perform Nurse Action F, but not nurse actions A, B, C, D, or E. Further consulting FIG. 5, the care giver slides the sliding card to an Activity rating of 2 and follows the arrows and protocols indicated in the view window (namely Nurse Action K, but not Nurse Action J since the Braden Scale total score is 15 for this patient). The care giver then slides the sliding card until the grade of 3 for nutrition number is indicated in the view window. The care giver then follows protocols indicated in the Nurtition window. For the patient above, given that the patient is only fed orally, Nurse Action P would be performed by the care giver, but not Nurse Actions 0 or V. The care giver then consults the Friction and Shear section of FIG. 5. Noting that a score of 3 for Friction & Shear does not appear with any arrows, no further Nurse Action protocols need be performed. Thus, for the patient of this example, as shown in the Nurse Action Report Sheet (FIG. 6), Nurse Action protocols F, K and P should be performed by the care giver.

Table 3: Possible Text for Modular Wound Prevention Protocol Sheet (FIG. 6)

Nurse Action Report Circle or check off the appropriate treatments and indicate products used.

TABLE 3

Section 1: Managing Moisture

A. If related to tube feeding, lower volume, increase delivery time, decrease osmolality, add filler or add bulking agent. (Consult dietary plan). If nutritional intake is entreal, determine potential causes of loose stool. Check for impaction. If frequent, apply fecal incontinence pouch. If persistent, obtain order for anti-diarrheal medication.
☐ Products used
_____
_____

B. Cleanse skin promptly and thoroughly with incontinence skin cleanser or non-drying soap and pat dry.
☐ Aloe Vesta Perineal Solution
☐ Aloe Vesta Perineal Foam
☐ Other_____
_____

C. If taking diuretic, schedule in late afternoon. If moisture is due to regular nighttime urinary incontinence, consider one scheduled toileting during the night.
_____
_____

D. Implement q 2 h toileting schedule (waking hours) and offer fluids every 2 hours during waking hours. Cleanse skin promptly with non-drying soap or incontinence skin cleanser, pat dry. Use moisture barrier to protect skin. Use only underpads that wick fluid away from the skin, leaving surface next to skin dry. Cleanse skin, incontinence cleanser or non-drying soap.
☐ Aloe Vesta Perineal Solution
☐ Aloe Vesta Perineal Foam
☐ Aloe Vesta Protective Ointment
☐ Other_____

E. Use moisture barrier to protect surrounding tissue. Pouch heavily draining wound (Consult ET).
☐ Aloe Vesta Protective Ointment
☐ Other_____

F. Check linens every two hours. Change linens as needed. Bathe daily to remove waste products left by perspiration. Clean skin folds thoroughly, but gently and pat dry. Consider different mattress or support surface if a non-breathable covering is aggravating problem.
☐ Septi Soft Body Wash & Shampoo
☐ Other_____

Section 2: Activity

G. Implement plans for small shift in position.
_____
_____

H. Use pressure reducing chair seating. Implement q 1 h chair repositioning schedule.
☐ Positioning Cushion
I. Teach patient to do lift-off's 15 minutes.
_____

J. When in bed, use foam wedges for lateral position and pillow to bridge sacrum. Avoid lateral positioning of more than 30 degrees.
☐ Positioning Cushion
☐ Pillow
☐ Other_____
K. Place pressure reducing surface on bed or chair. Avoid positioning directly on trochanter.
☐ Mattress Overlay
☐ Positioning Cushion
☐ Other_____

L. When in bed, use positioning devices to suspend heels so they do not touch the mattress. Use good positioning to keep knees from touching. Avoid elevating HOB more than 30 degrees, except for brief periods.
☐ Positioning Cushion
☐ Other_____
M. Use pressure reducing chair seating. Implement q 1 h chair repositioning schedule.
☐ Positioning Cushion
☐ Other_____
N. Implement q 2 h turning schedule. If patient can make purposeful movements, encourage frequent turning/shifts in body position.
_____

TABLE 3-continued

Section 3: Managing Nutrition

O. If dietician was not consulted to determine the match between the patient condition, metabolic need, and formula type and amount-initiate dietary consult to do so now.

P. Give protein supplement at bedtime.
☐ Protein Supplement
Q. If the patient is receiving less than optional amount because of high residual volumes in stomach, notify physician and obtain medication orders to decrease gastric retention or obtain orders for parental nutrition.
If the patient is receiving less than the optimal amount because of inadequate ordering or changes in patient's condition, request new orders from physician or dietician.

R. Request order for multi-vitamin with Vitamins A, C, and Zinc. Obtain dietary consult if these interventions are not successful within 24 hours. Change diet to reflect food preferences/habits or to address any problems with chewing or swallowing. Create caloric intake plan and monitor goal achievement.
☐ Vitamin Supplement
S. Attempt protein supplement at meals and before bedtime.
☐ Protein Supplement
T. Give supplement twice a day.
☐ Protein Supplement
☐ Other_____
U. Initiate physician contact to clarify goals of treatment and/or to examine avenues to improve nutritional intake.

V. Reassess periodically if patient's condition changes.

Section 4: Friction & Shear

W. Avoid raising HOB > 30 degrees. Use lifting sheet to move patient in bed; do not drag patient across the linens. Use elbow and heel protectors if these prominences are exposed to friction. Use a sheepskin under spastic extremities. (Do not place under trunk.)
☐ Positioning Cushion
☐ Heel or Elbow Protectors
X. Consider a trapeze, if patient has sufficient upper body strength to assist in moves.
Patient_____  Date:_____
Nurse_____  Physician_____
Notes_____

Further information for products referred to in the above table is listed below.

AQUACEL Hydrofiber: a wound dressing comprising a non-woven pad composed of sodium carboxymethyl-cellulose fibers. The dressing is highly absorbent and forms a soft gel interacts with wound exudate and forms a soft gel which maintains a moist environment for wound healing.

Arthropad: Tubigrip Arthropad is a wrapping bandage designed to provide lasting, effective support with complete freedom of movement for the patient. The Tubigrip Arthropad provides tissue support in the management of soft-tissue injuries and general edema and may be used as a pressure dressing.

Carboflex Odor: A sterile non-adhesive dressing with an absorbent wound contact layer (containing Alginate and Hydrocolloid), an activated charcoal pad and a smooth water-resistant top layer.

DuoDERM Extra Thin: highly flexible, control gel formula dressing made for use on dry to lightly exudating wounds. The dressing conforms to the body, cleans by autolytic debridement and is a highly effective secondary dressing for wound fillers.

DuoDERM Hydroactive Gel: a sterile gel comprising natural hydrocolloids (pectin, sodium carboxymethyl-cellulose) in a clear, viscous vehicle.

DuoDERM Hydroreactive Gel: a sterile gel composed of natural hydrocolloids (pectin, sodium carboxymethyl-cellulose) in a clear, viscous vehicle. This product is designed for the management of partial and full-thickness wounds and creates a moist healing environment around a wound which helps to promote the natural autolytic process of debridement.

DuoDERM CGF: is a dressing that interacts with wound exudate to produce a soft mass that enables removal of the dressing with little or no damage to newly formed tissues. The dressing helps isolate the wound against bacterial, viral (HIV-1 and HBV) and other external contamination and can remain in place up to seven days.

Kaltostat: a sterile non-woven dressing of calcium-sodium alginate fiber which can absorb wound exudate or saline and convert from a firm gel/fiber mat. The gel forms a moist, warm environment at the wound interface.

Kalostat Dressing: a highly absorbent calcium alginate dressing derived from natural seaweed designed to absorb exudate and control minor bleeding. The dressing is easy to apply, can remain in place up to seven days, and may be used on moderately to heavily exuding wounds.

Lyofoam Foam Dressing: A polyurethane foam dressing comprising an absorptive hydrophilic contact surface and a secondary outer foam layer through which the aqueous component can be lost by evaporation. The dressing is freely permeable to gases and water vapor but resists strike-through of aqueous solutions and exudate, as the outer layer has hydrophobic properties.

SAF Gel: an alginate containing formulation designed for multiple uses. The gel is indicated for use on chronic and acute wounds such as dry wounds, pressure ulcers (Stages I to IV) and stasis ulcers.

SAF Clens: a wound cleaner that has a dual surfactant formulation designed for cleansing of chronic wounds, including superficial, partial-thickness, dry or nectotic wounds. The wound cleanser is nontoxic, noniritating and comes in no-rinse formula.

Signadress: a hydrocolloid dressing comprising an inner (wound contact) layer of hydrocolloids contained within an adhesive polymer matrix and an outer layer of polyurethane film. The dressing also has a product identification mark (ConvaTec registered tear drop trademark) and a visible (SignaDRESS) change indicator guide printed on the film backing.

Sure Press High Compression Bandage and Sure Press Absorbant Padding: The SurePress High Compression Bandage System is comprised of two layers: the SurePress High Compression Bandage, a washable bandage made from high-quality blend of cotton-viscose, nylon and LYCRA, and the SurePress Absorbent Padding for use as an underlayer. The System can be used for management of venous leg ulcers and associated conditions, and is contraindicated for the management of arterial and mixed venous/arterial ulcers and legs with an ankle circumference less than 18 cm.

Tubipad: is made from a layer of polyurethane foam banded to a length of elastic tubular bandage that is used for the protection of heels, elbows and knees.

UNNA-FLEX: is an elastic bandage that provides compression, for instance to improve venous return. The bandage can be self-adherent or in the form of a boot.

One will appreciate that products listed in the table above, or functional equivalents, are commercially available from a variety of vendors.

All publications and references, including but not limited to patents and patent applications, cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for publications and references.

While this invention has been described with an emphasis upon preferred embodiments, it will be obvious to those of ordinary skill in the art that variations in the preferred devices and methods may be used and that it is intended that the invention may be practiced otherwise than as specifically described herein. Accordingly, this invention includes all modifications encompassed within the spirit and scope of the invention as defined by the claims that follow.

What is claimed:

1. A method of identifying a wound care protocol for a given wound or wound prevention protocol appropriate for a given patient comprising:
   classifying the wound or patient against a defined scale for a first wound factor, which is a defined wound assessment factor or defined wound risk assessment factor to obtain a wound classification;
   grading the wound or patient against defined scales for one or more second wound factors, which are wound assessment factors or wound risk assessment factors; and
   operating a mechanical visual decision tree device to show a decision or visual decision tree corresponding to the wound classification or to a scale for a wound assessment factor, wherein the visual decision tree device identifies at least one component of a treatment protocol for the graded wound factors.

2. The method of claim 1, wherein at least one visual decision tree indicates two or more distinct decisions based on the grade of one or more second wound factors.

3. A method of claim 1 of identifying a wound care protocol appropriate for a given wound comprising:
   classifying the wound against a defined wound classification scheme;
   grading the wound against defined scales for one or more second wound assessment factors; and
   operating visual decision tree device to show a decision or visual decision tree corresponding to the wound classification or to a grade for a wound assessment factor, wherein at least one visual decision tree produced by the device dictates two or more distinct decisions based on the grade of one or more second wound assessment factors, and wherein the visual decision device identifies a treatment protocol for the wound classification and grades of the second wound assessment factors.

4. The method of claim 3, wherein one of the two visual decision tree devices is selected based on wound classification, and the selected visual decision tree device is operated to show a decision or decision tree corresponding to a grade for exudate amount.

5. The method of claim 3, wherein the wound classification scheme grades wounds from non-open or closed wounds, to wounds of various thicknesses, to wounds that cannot be graded due to obstructions.

6. The method of claim 1, further comprising:
   providing an interactive visual scoring sheet on which markers for the available scores for two or more wound factors are displayed; and
   marking the appropriate score for the two or more wound factors on the interactive visual scoring sheet,
   wherein the interactive visual scoring sheet contains a marker associated with one or more of the scores identifying an addition to the treatment protocol.

7. A visual decision tree device for identifying a wound care protocol for a given wound or wound prevention protocol appropriate for a given patient comprising:
   a mechanical device for identifying and displaying one of at least two decisions or visual decision trees based on one or more inputted wound factors according to a defined scale,
   wherein the visual decision tree device identifies at least one component of a treatment protocol for the graded wound factors;
   and wherein the mechanical device comprises at least one card on which the decisions or visual decision trees and values for a wound factor are printed; and
   a sleeve in which the card slides having at least two openings, the first opening alignable separately with separate wound factor values, and the second opening alignable with the distinct decisions on visual decision trees depending on the alignment with the first openings.

8. The visual decision tree device of claim 7 wherein the card comprises markers corresponding to a defined scale for classifying the wound or patient.

9. The visual decision tree device of claim 7 wherein one or more cards shows a visual decision tree and wherein the housing comprises a view window through which one or more visual decision trees corresponding to the wound classification can be viewed.

10. A method of identifying a wound prevention protocol appropriate for a given patient comprising:
- classifying the patient against a defined scale for a first wound risk assessment factor to obtain a wound classification;
- grading the patient against defined scales for one or more second wound risk assessment factors; and
- operating a mechanical visual decision tree device to show a decision or visual decision tree corresponding to a scale for a wound risk assessment factor, wherein the visual decision tree device identifies at least one component of a treatment protocol for the graded wound risk assessment factors.

* * * * *

UNITED STATES PATENT AND TRADEMARK OFFICE
CERTIFICATE OF CORRECTION

| | |
|---|---|
| PATENT NO. | : 7,184,963 B2 |
| APPLICATION NO. | : 09/487944 |
| DATED | : February 27, 2007 |
| INVENTOR(S) | : Ronald Shannon |

It is certified that error appears in the above-identified patent and that said Letters Patent is hereby corrected as shown below:

column 18, line 4 - "Actions 0" should read --Actions O--

In the Claims:

Insert Claim 11 -

--11. A method of identifying a wound care protocol for a given wound or wound prevention protocol appropriate for a given patient comprising:
 classifying the wound or patient against a defined scale for a first wound factor, which is a defined wound assessment factor or defined wound risk assessment factor to obtain a wound classification;
 grading the wound or patient against defined scales for one or more second wound factors, which are wound assessment factors or wound risk assessment factors;
 operating a mechanical visual decision tree device to show a decision or visual decision tree corresponding to the wound classification or to a scale for a wound assessment factor, wherein at least one visual decision tree dictates two or more distinct decisions based on the grade of one or more second wound factors, and wherein the visual decision tree device identifies at least one component of a treatment protocol for the graded wound factors; and
 marking a pre-defined display of treatment protocols to identify the components of a treatment protocol identified by the method.--

Signed and Sealed this

Eighteenth Day of March, 2008

JON W. DUDAS
*Director of the United States Patent and Trademark Office*

UNITED STATES PATENT AND TRADEMARK OFFICE
CERTIFICATE OF CORRECTION

PATENT NO. : 7,184,963 B1 Page 1 of 1
APPLICATION NO. : 09/487944
DATED : February 27, 2007
INVENTOR(S) : Ronald Shannon It is certified that error appears in the above-identified patent and that said Letters Patent is hereby corrected as shown below:

column 18, line 4 - "Actions 0" should read --Actions O--

In the Claims:

Column 24, line 5
Insert Claim 11 -

--11. A method of identifying a wound care protocol for a given wound or wound prevention protocol appropriate for a given patient comprising:
    classifying the wound or patient against a defined scale for a first wound factor, which is a defined wound assessment factor or defined wound risk assessment factor to obtain a wound classification;
    grading the wound or patient against defined scales for one or more second wound factors, which are wound assessment factors or wound risk assessment factors;
    operating a mechanical visual decision tree device to show a decision or visual decision tree corresponding to the wound classification or to a scale for a wound assessment factor, wherein at least one visual decision tree dictates two or more distinct decisions based on the grade of one or more second wound factors, and wherein the visual decision tree device identifies at least one component of a treatment protocol for the graded wound factors; and
    marking a pre-defined display of treatment protocols to identify the components of a treatment protocol identified by the method.--

This certificate supersedes the Certificate of Correction issued March 18, 2008.

Signed and Sealed this

Fifteenth Day of April, 2008

JON W. DUDAS
*Director of the United States Patent and Trademark Office*